(12) United States Patent  (10) Patent No.: US 8,052,710 B2
Kambin et al.  (45) Date of Patent: Nov. 8, 2011

(54) ENDOSCOPIC BALLOON TISSUE DISSECTOR AND RETRACTOR

(76) Inventors: Parviz Kambin, Devon, PA (US); Sheila P. Kambin, Broomall, PA (US)

( * ) Notice: Subject to any disclaimer, the term of this patent is extended or adjusted under 35 U.S.C. 154(b) by 682 days.

(21) Appl. No.: 11/639,869

(22) Filed: Dec. 15, 2006

(65) Prior Publication Data

US 2008/0147109 A1 Jun. 19, 2008

(51) Int. Cl.
*A61M 29/00* (2006.01)

(52) U.S. Cl. ...................................................... 606/192

(58) Field of Classification Search .................. 606/192, 606/208, 174, 205, 206, 207; 600/215, 217, 600/219, 210
See application file for complete search history.

(56) References Cited

U.S. PATENT DOCUMENTS

| | | | |
|---|---|---|---|
| 817,973 A | 4/1906 | Hausmann | |
| 2,202,748 A | 4/1938 | James | |
| 2,689,568 A | 8/1952 | Wakefield | |
| 3,162,190 A | 12/1964 | Del Gizzo | |
| 4,459,978 A | 7/1984 | Kotsanis | |
| 4,779,611 A | 10/1988 | Grooters et al. | |
| 5,029,574 A | 7/1991 | Shimamura et al. | |
| 5,273,026 A | 12/1993 | Wilk | |
| 5,293,863 A * | 3/1994 | Zhu et al. | 600/214 |
| 5,607,441 A | 3/1997 | Sierocuk et al. | |
| 5,616,117 A | 4/1997 | Dinkler et al. | |
| 5,707,382 A | 1/1998 | Sierocuk et al. | |
| 5,728,119 A | 3/1998 | Smith et al. | |
| 5,762,604 A * | 6/1998 | Kieturakis | 600/115 |
| 5,776,054 A | 7/1998 | Bobra | |
| 5,944,734 A | 8/1999 | Hermann et al. | |
| 6,007,483 A | 12/1999 | Kieturakis | |
| 6,074,343 A | 6/2000 | Nathanson et al. | |
| 6,168,608 B1 | 1/2001 | Echeverry et al. | |
| 6,214,028 B1 * | 4/2001 | Yoon et al. | 606/205 |
| 6,248,062 B1 | 6/2001 | Adler et al. | |
| 6,371,968 B1 * | 4/2002 | Kogasaka et al. | 606/190 |
| 6,379,351 B1 * | 4/2002 | Thapliyal et al. | 606/41 |
| 6,451,042 B1 | 9/2002 | Bonutti | |
| 6,596,010 B1 | 7/2003 | Hermann et al. | |
| 6,821,247 B2 | 11/2004 | Vierra et al. | |
| 7,037,317 B2 | 5/2006 | Hermann et al. | |
| 2004/0225317 A1 * | 11/2004 | Rehnke | 606/190 |
| 2006/0106288 A1 | 5/2006 | Roth et al. | |
| 2006/0122462 A1 | 6/2006 | Roth et al. | |
| 2006/0293692 A1 * | 12/2006 | Whipple et al. | 606/104 |

* cited by examiner

*Primary Examiner* — Tom Hughes
*Assistant Examiner* — Tin Nguyen
(74) *Attorney, Agent, or Firm* — Howson & Howson LLP

(57) ABSTRACT

An instrument for endoscopic surgery comprises a retractor having independently spreadable retractor blades pivotally mounted at the distal end of a tube, through which a balloon dissector can be passed. The blades are pivoted on axes transverse to the elongation of the tube. The blades are externally convex and internally concave in cross-sectional planes to which the elongation of the tube is perpendicular. The balloon is transparent, and the balloon dissector is provided with an image transmitter for visualization of tissue dissection.

15 Claims, 8 Drawing Sheets

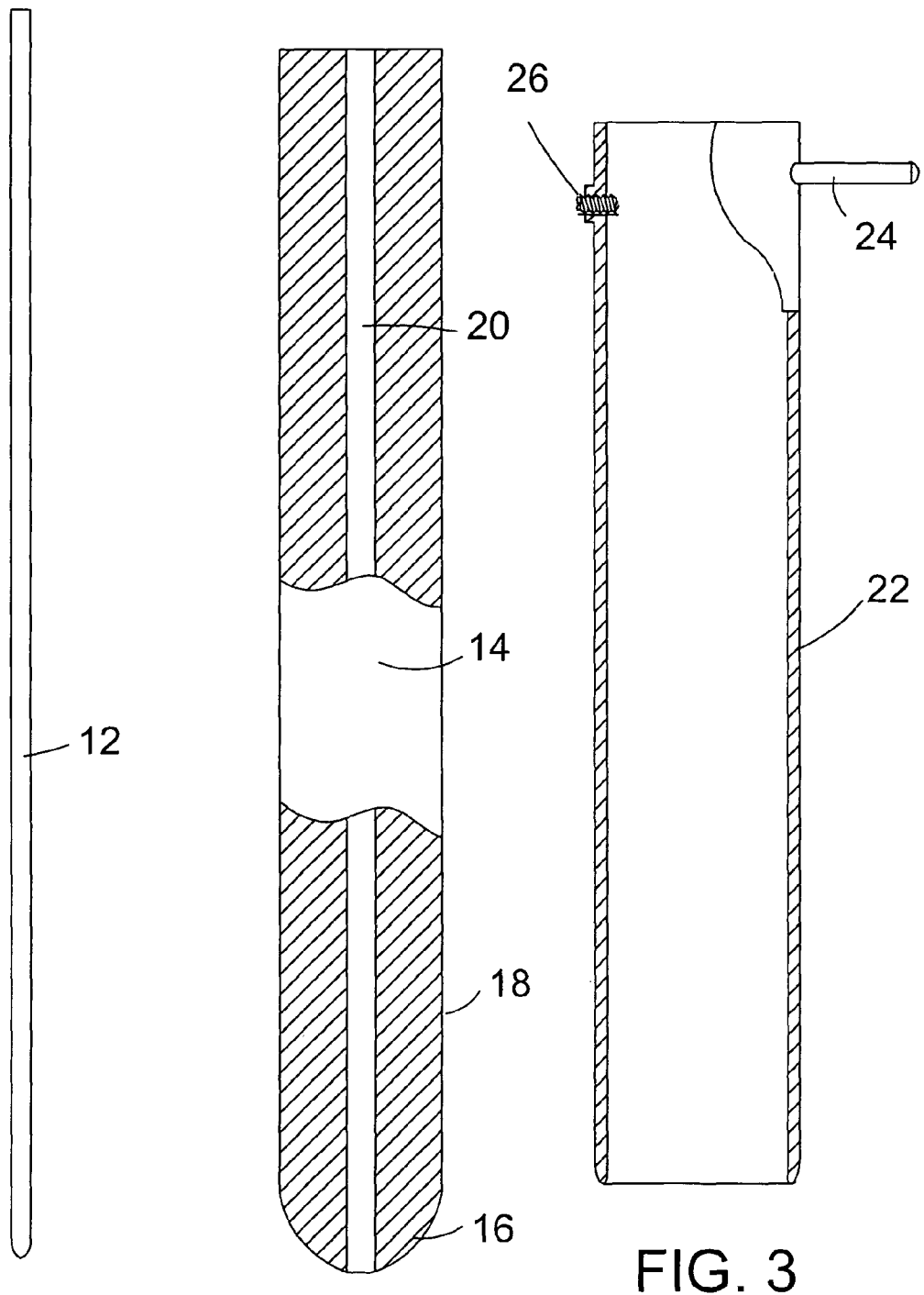

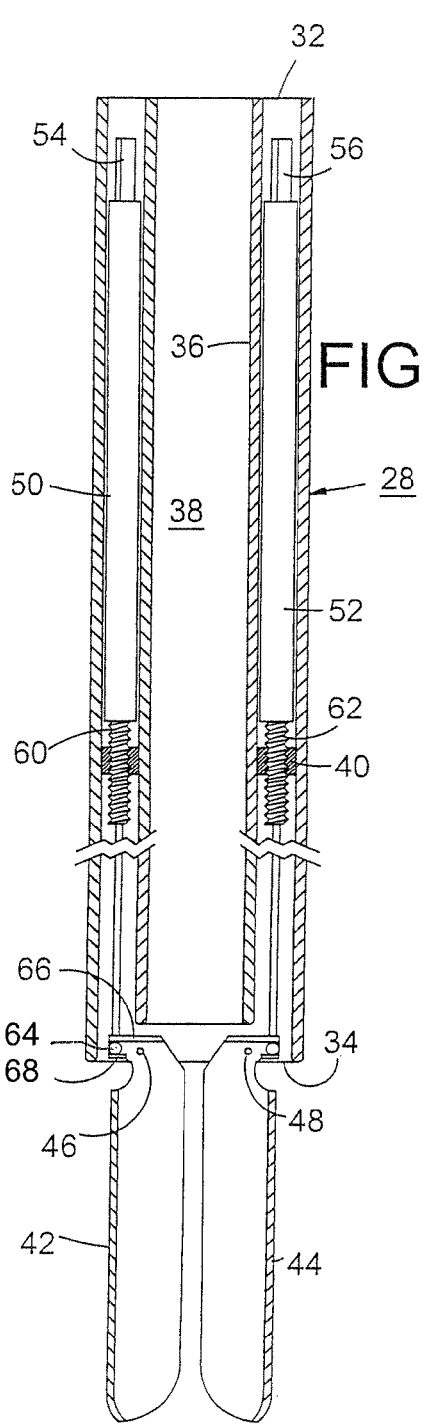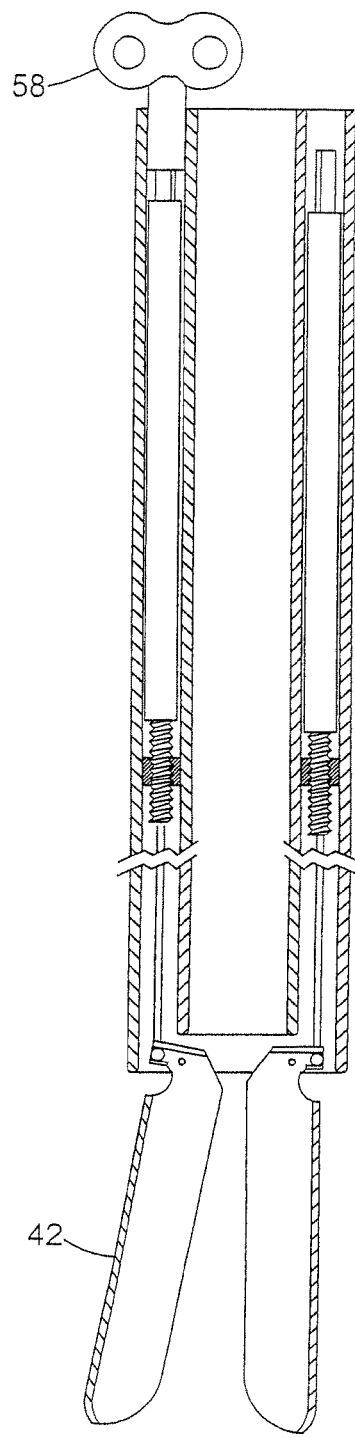

ENDOSCOPIC BALLOON TISSUE DISSECTOR AND RETRACTOR

FIELD OF THE INVENTION

This invention relates to surgery, and particularly to instruments for dissection and retraction of tissue in endoscopic surgery.

BACKGROUND OF THE INVENTION

In surgery, adhesions and scar tissue, formed in a patient's thoracic or abdominal cavity as a result of previous surgery, infection or trauma, frequently cause difficulties in locating, and gaining access to, the internal organs or structures that require repair or removal. For example, adhesions frequently cause problems in anterior and anterolateral access to the spinal column or the content of the abdominal cavity.

Typically, a surgeon releases adhesions manually, using a gloved finger. However, when a gloved finger is used, it is not possible to visualize the adhesions, and unnecessary bleeding, and tearing, or damage to the normal anatomy, almost inevitably occurs. In addition, access to certain organs requires the identification and separation of two muscle groups through their anatomical planes.

An endoscopic balloon tissue dissector can be used to achieve the above objectives, and various instruments incorporating inflatable balloons have come into use for tissue dissection. The balloon, incorporated at the distal end of an endoscopic instrument, is inserted between adjacent tissue layers, and inflated to separate those layers. Alternatively, for dissection with visualization, some surgeons have used an "optical trocar," which comprises a tube having a system of lenses or a bundle of optical fibers for transmitting an image from the distal end of the tube to an eyepiece or to an electronic video monitor.

More recently, a surgical dissector has been developed which combines features of the balloon dissector and the optical trocar. Such an instrument is described in U.S. Pat. No. 5,607,441. In that instrument, a transparent, inflatable, dissecting balloon is provided at the distal end of a shaft, and an optical instrument, extending through the shaft into the interior of the balloon, enables the surgeon to visualize the dissection as it takes place.

Despite the advances in endoscopic surgery exemplified by U.S. Pat. No. 5,607,441 and numerous other patents, there remains a need for instrumentation that can achieve dissection of tissue and provide optimal access to a surgical site with minimal trauma to the patient.

BRIEF SUMMARY OF THE INVENTION

In a preferred embodiment of the invention, the instrument comprises an elongated tube having proximal and distal ends, and an internal passage for insertion of an instrument through the tube. Plural retractor blades, preferably two opposed retractor blades, extend distally from a location adjacent the distal end of the tube, and are movable radially with respect to the central axis of the tube by adjuster rods. An adjuster rod is connected to each blade, extends proximally at least part way through the tube, and is accessible at a location adjacent the proximal end of the tube for independent radial adjustment of the retractor blades.

Preferably, each of the retractor blades is pivoted at a pivot location adjacent the distal end of the elongated tube, and the adjuster rod connected to each blade is connected at a location spaced from the pivot location of the blade, so that it can effect radial adjustment by pivoting the blade to which it is connected.

The elongated tube preferably has a substantially cylindrical external surface substantially symmetrical about its central axis, and the internal passage is also substantially symmetrical about the central axis. In this embodiment, the plural retractor blades consist of two retractor blades in opposed relationship to each other, and the blades are adjustable to positions in which they are substantially within an axial projection of the substantially cylindrical external surface of the tube but substantially entirely external to an axial projection of the internal passage. Consequently, an expandable balloon on an end of a balloon dissector can be inserted through the internal passage so that it can project distally beyond the blades, and withdrawn, while the blades are in the above-mentioned positions.

The blades are preferably formed so that they have outer, tissue-engaging, surfaces which are convex throughout substantially their entire axial lengths in cross-sectional planes to which the central axis is perpendicular, and inner surfaces which are concave throughout substantially their entire axial lengths in the same cross-sectional planes.

The adjusting rods preferably have external screw threads threadingly engaged with internal screw threads fixed to the tube, and are preferably separated from the internal passage by a second tube defining the internal passage.

Another aspect of the invention is an instrument in which the tube having retractor blades at its distal end is combined with a balloon dissector. More particularly, this combined instrument comprises an elongated first tube having proximal and distal ends, the tube having an internal passage for insertion of an instrument through the tube. The first tube has a substantially cylindrical external surface substantially symmetrical about an axis of elongation of the tube, and the internal passage is also substantially symmetrical about the same axis. Two retractor blades, in opposed relationship to each other, extend distally from locations adjacent the distal end of the first tube and are movable radially with respect to the axis tube's axis of elongation. An adjuster rod is connected to each blade, and each rod extends proximally at least part way through the first tube, and is accessible at a location adjacent the proximal end of the first tube for independent radial adjustment of the retractor blades. The balloon dissector comprises an elongated second tube having proximal and distal ends, and an expandable balloon at the distal end of the second tube. The blades are adjustable to positions in which they are substantially within an axial projection of the external surface of the first tube but substantially entirely external to an axial projection of the second tube and any external channel-defining wall on the second tube. The second elongated tube, that is, the tube of the balloon dissector, extends through the internal passage of the first elongated tube from a location proximal with respect to the proximal end of the first elongated tube to a location at which at least part of the expandable balloon is distal with respect to the blades. Thus, the balloon can be expanded to dissect tissue located in distal relation to the blades, and then contracted to permit movement of the blades into a space created by the dissection of tissue by the balloon. Then spreading of the tissue can be effected by adjustment of the blades, and, following withdrawal of the second elongated tube, another instrument can be introduced through the internal passage of the first tube for surgery on the anatomical structure exposed by dissection and spreading.

Here again, each of the two opposed retractor blades is preferably pivoted at a pivot location adjacent the distal end of the elongated tube, and the adjuster rod connected to each blade is connected at a location spaced from the pivot location of the blade so that it can effect radial adjustment by pivoting the blade to which it is connected.

The balloon of the balloon dissector is preferably transparent, and a shaft, extending through the second elongated tube to a location within the balloon, comprises an image transmitter for transmitting a visual image of a patient's anatomical structure immediately external to the balloon, through the elongated first tube, to a location external to the patient.

Still another aspect of the invention is a surgical method which can be carried out using the above-described instruments. The method comprises at least the following steps. A first step is the percutaneous introduction of an elongated first tube having proximal and distal ends, the tube having an internal passage for insertion of an instrument through the tube, and two retractor blades in opposed relationship to each other and extending distally from the distal end of the tube. Then, a balloon, connected to a distal end of an elongated second tube extending through the internal passage of the first tube, is disposed at a location distal with respect to the retractor blades, and expanded by introducing a fluid, which may be either a liquid or a gas, into the interior of the balloon. By expanding the balloon the surgeon can dissect tissue at the location of the balloon. Afterwards, by at least partially contracting the balloon, and moving the elongated first tube in the distal direction, the surgeon can cause the blades to move into the space created by the dissection of tissue using the balloon. The dissected tissue can then be spread by moving at least one of the blades apart from the other before, during, or after withdrawal of the elongated second tube from the internal passage of the elongated first tube. After withdrawal of the second tube, and, while using the blades to maintain the dissected tissue in a spread condition, another instrument can be introduced through the internal passage of the first tube for surgery on anatomical structure exposed by the dissection and spreading steps.

If the balloon is transparent, during the step of expanding the balloon, tissue at the location of the balloon can be visualized through the balloon by transmitting an image of tissue at the location of the balloon through an image transmitter in a shaft extending through the elongated second tube to the interior of the balloon.

The image transmitter can also be used for visualization during expansion of the retractor blades. If the blades are independently adjustable, in the spreading step, at least one blade can be moved apart from the other blade independently of movement of the other blade. In this way, tissue can be spread for access to a surgical site with minimal trauma to the patient.

The step of percutaneously introducing an elongated first tube can be carried out by a series of steps including the steps of passing an obturator having a blunt tip through a patient's skin, passing a hollow cannula over the obturator, withdrawing the obturator, and introducing the elongated first tube through the hollow cannula. The obturator can have a guide-wire channel, and can be introduced by passing it over a pointed guide wire previously passed through the patient's skin.

Other details and advantages of the invention will be apparent from the following detailed description when read in conjunction with the drawings.

BRIEF DESCRIPTION OF THE DRAWINGS

FIG. 1 is an elevational view of a guide wire which can be used in the surgical dissection of tissue in accordance with the invention;

FIG. 2 is an elevational view, partly in section, of a blunt-tipped cannula, having a longitudinal guide wire-receiving channel;

FIG. 3 is an elevational view, partly in axial cross-section, of a hollow cannula;

FIG. 4 is a shortened axial section of an elongated first tube in accordance with the invention, the tube having retractor blades shown in positions in which they are substantially within an axial projection of the external surface of the tube;

FIG. 5 is a shortened axial section, similar to FIG. 5, but showing one of the retractor blades in a spread condition;

DETAILED DESCRIPTION OF THE PREFERRED EMBODIMENT

Figure 6:
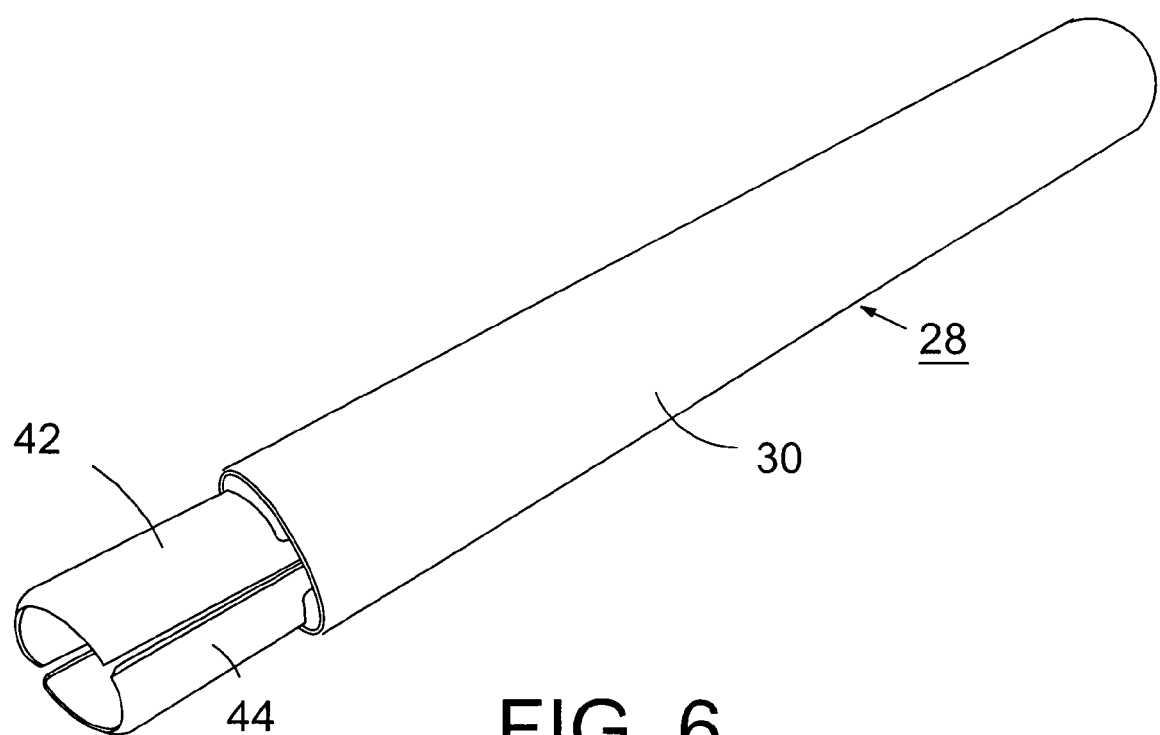
FIG. 6 is a perspective view of the first elongated tube, showing the retractor blades in the same condition as shown in FIG. 4.

FIG. 1 shows a guide wire 12, which is typically inserted through an incision in a patient's skin and advanced toward the site at which surgery is to be performed. For example, in the case of spinal surgery performed using a posterior or posterolateral approach, the guide wire can be inserted through the patient's skin, using fluoroscopic guidance to avoid tissue damage. With the guide wire 12 in place, an obturator 14, as shown in FIG. 2, is passed over the guide wire. The obturator is elongated, has a blunt tip 16, a preferably circular, cylindrical exterior wall 18, and a centrally located longitudinal channel 20 for receiving the guide wire 12. As an alternative, a solid obturator can be used without a guide wire, especially in cases where the depth to which the obturator is inserted is small.

With the obturator 14 in place, a cannula 22, as shown in FIG. 3 can be passed over the exterior of the obturator. The cannula can be manipulated by a handle 24, which can also be rigidly attached by a support arm to the operating table or another fixed structure. A set screw 26 is provided in the wall of the cannula for holding the tube of a retractor in fixed relation to the cannula so that the retractor does not slide forward or backward during surgery.

As shown in FIG. 4, the retractor 28 comprises an elongated outer tube 30 having a proximal end 32, a distal end 34, and a substantially cylindrical, preferably circular, outer surface symmetrical about a central axis extending lengthwise of the tube. An inner elongated tube 36, which is coaxial with the first tube, is located inside the first tube. The inner tube 36 is also preferably symmetrical about the axis of tube 30, and its inner wall, which is preferably also substantially cylindrical and circular, forms an internal passage 38, though which another instrument can be inserted.

The inner and outer tubes are held in fixed relationship to each other by a ring 40, and by other connecting elements (not shown).

Two retractor blades, 42 and 44, extend in the distal direction from the distal end 34 of tube 30 in opposed relationship to each other. The blades are pivoted on pins 46 and 48, respectively, and are independently movable about their pivot axes so that one or both can be moved radially outward relative to the central axis of the tubes. Blade 42 is shown pivoted outward in FIG. 5, while blade 4 remains in its original position.

The shapes of the blades can be better appreciated from FIG. 6, in which it can be seen that the blades have convex outer surfaces and concave inner surfaces. That is, the blades have outer, tissue-engaging, surfaces which are convex throughout substantially their entire axial lengths in cross-sectional planes to which the axis of the tubes is perpendicular, and inner surfaces which are concave throughout substantially their entire axial lengths in the same cross-sectional planes. Because of the concave/convex shapes of the blades, when they are in the positions depicted in FIG. 4, they are located substantially entirely between axial projections of the inner passage and the outer wall of tube 30. More particularly, the blades are adjustable to positions in which they are substantially within an axial projection of the substantially cylindrical external surface of the elongated first tube, but substantially entirely external to an axial projection of the internal passage 38. When the blades are in the positions shown in FIG. 4, it is possible for the retractor to be inserted through the cannula 3 (FIG. 3), and it is also possible for an instrument having a width nearly equal to the width of passage 38 to be inserted, without interference, through passage 38 and through the space between the blades.

The blades are adjustable independently by rods 50 and 52, which extend through the space between tubes 30 and 36. The rods have non-circular proximal end extensions 54 and 56 near the proximal end 32 of the outer tube 30. These extensions are engageable by a key 58 (FIG. 5) for rotation of the rods to adjust the positions of the blades 42 and 44. Threads 60 and 62, formed on the rods, are threadingly engaged with internal threads formed in ring 40, which is fixed to both tubes. A ball, formed at the distal end of each rod, fits between upper and lower plates formed on the blade with which the rod is associated at a location spaced a short distance from the pivot pin. For example rod 50 is provided with a ball 64, and extends through a hole in upper plate 66 of blade 42 and fits in a space between the upper plate 66 and a lower plate 68. Upon rotation of the rod in one direction, the rod will pull up on plate 66, causing the blade 42 to pivot outward. Upon rotation of the rod in the opposite direction, the rod will push on plate 68 causing the blade 42 to pivot inward. The pitch of the threads of the threaded rods and the ring is preferably sufficiently small that the blades cannot be moved about their pivots by forces applied directly to the blades.

Figure 7:
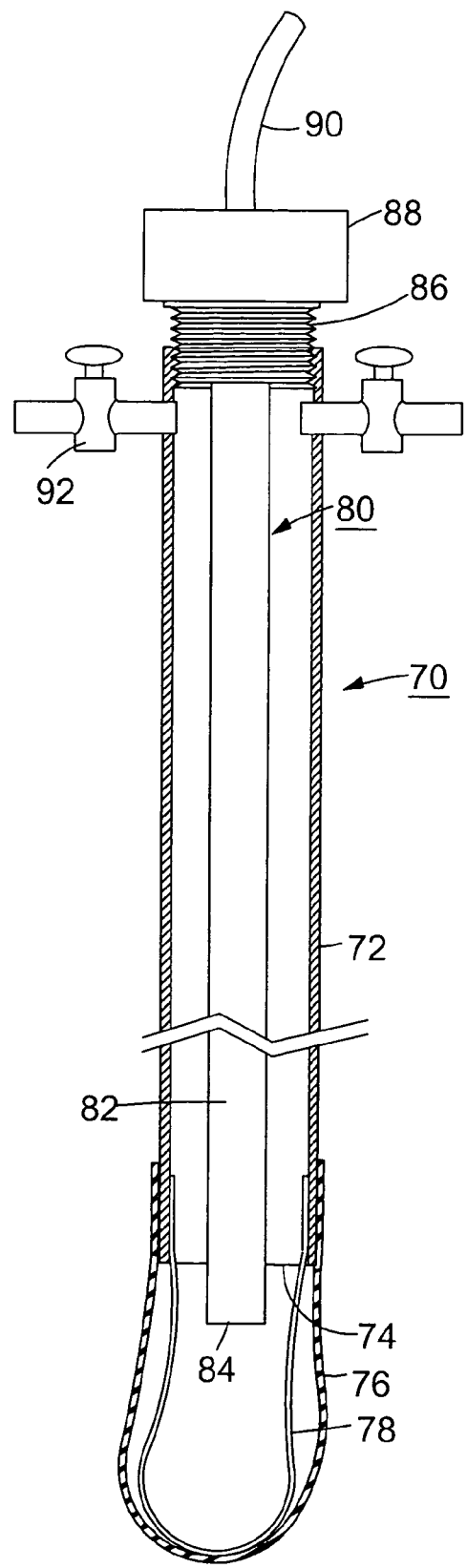
FIG. 7 is a shortened axial section of an elongated second tube, having a dissecting balloon at one end, and an image transmitting shaft extending through the tube to the interior of the balloon.

The balloon dissector 70, shown in FIG. 7 comprises a second tube 72, the outer wall of which is preferably in the form of a circular cylinder having a diameter slightly less than that of the inner wall 38 of tube 36 (FIG. 4). Attached to the distal end 74 of the tube 72 is an expansible, preferably transparent, elastomeric balloon 76, which can be used to dissect tissue when expanded by introduction of a liquid or gas through tube 72. The balloon can be fabricated so that it expands uniformly, or so that it expands non-uniformly in a desired direction. A wire 78, which is flexible, but considerably more rigid than the balloon is located inside the balloon and also attached to the distal end of tube 72. The wire 78 aids the advancement of the unexpanded balloon into a patient's tissue, and is preferably made from metal or a fiber-reinforced polymer.

An image-transmitting device 80 is inserted through tube 72, and comprises an elongated shaft 82, the distal end 84 of which preferably extends beyond the distal end 74 of the tube into the interior of the balloon 78. The proximal end of the image transmitting device is provided with threads 86, which are threaded into the proximal end of the tube 72. In practice, tube 84 can be an optical telescope having a series of lenses arranged to focus an image onto a television camera 88, which is connected through a cable 90 to a monitor (not shown). Illumination at the distal end of the image transmitting device can be provided through an optical fiber bundle (not shown).

There are many alternatives to the image transmitting device described above. In one alternative version, the camera can be replaced by an eyepiece for direct viewing through the telescope. An optical fiber bundle can be used to transmit an image through shaft 82 either to a camera or to an eyepiece. As a further alternative, the camera can be situated at the distal end of shaft 82. In all cases, however, the image transmitter, when used in conjunction with the transparent balloon, enables the surgeon to visualize the tissue as it is dissected.

The balloon is expanded by the introduction of a fluid, preferably a normal saline solution, through valve 92, and through tube 72, into the interior of the balloon. Valve 94 is used for the removal of air bubbles from the saline solution, and may also be used for drawing saline solution out of tube 72.

Figure 8:
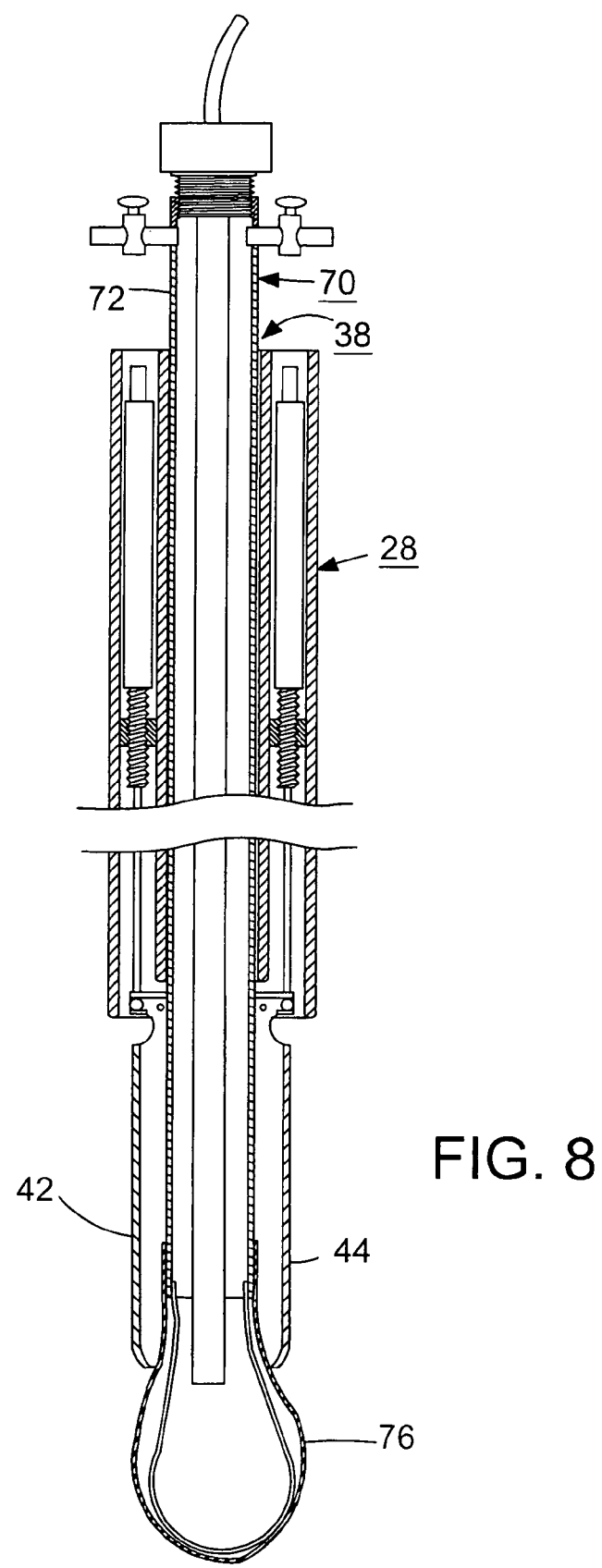
FIG. 8 is a shortened axial section showing the second tube extending through the first tube.

FIG. 8 shows the dissecting instrument of FIG. 7 inserted through the central passage of the retractor of FIGS. 4 and 5. At least part of the balloon 76 extends beyond the distal tips of the retractor blades 42 and 44. In this figure, it will be seen that tube 72 of the dissecting instrument fits through passage 38 of the retractor, and between the retractor blades 42 and 44, even though the retractor blades are not spread apart. When the blades are in the position shown, they are situated substantially entirely outside an axial projection of the inner wall of passage 38, but substantially entirely inside an axial projection of the outer wall of the outer tube. Consequently, with the blades in the position shown in FIG. 8, which is the same as the blade position shown in FIGS. 4 and 6, the retractor can be inserted through the hollow cannula 22 of FIG. 3. Moreover, without spreading the blades apart from each other, the balloon dissector 70 can be introduced through the passage 38, so that the balloon passes through the space between the blades to a location distal with respect to the tips of the blades, as shown in FIG. 8. Of course, the balloon dissector can be inserted either before or after the retractor is inserted through the cannula. However, ordinarily, the retractor will be inserted partway through the cannula, and temporarily locked in place by set screw 26 (FIG. 3), before the balloon dissector is inserted through the retractor.

Figure 9:
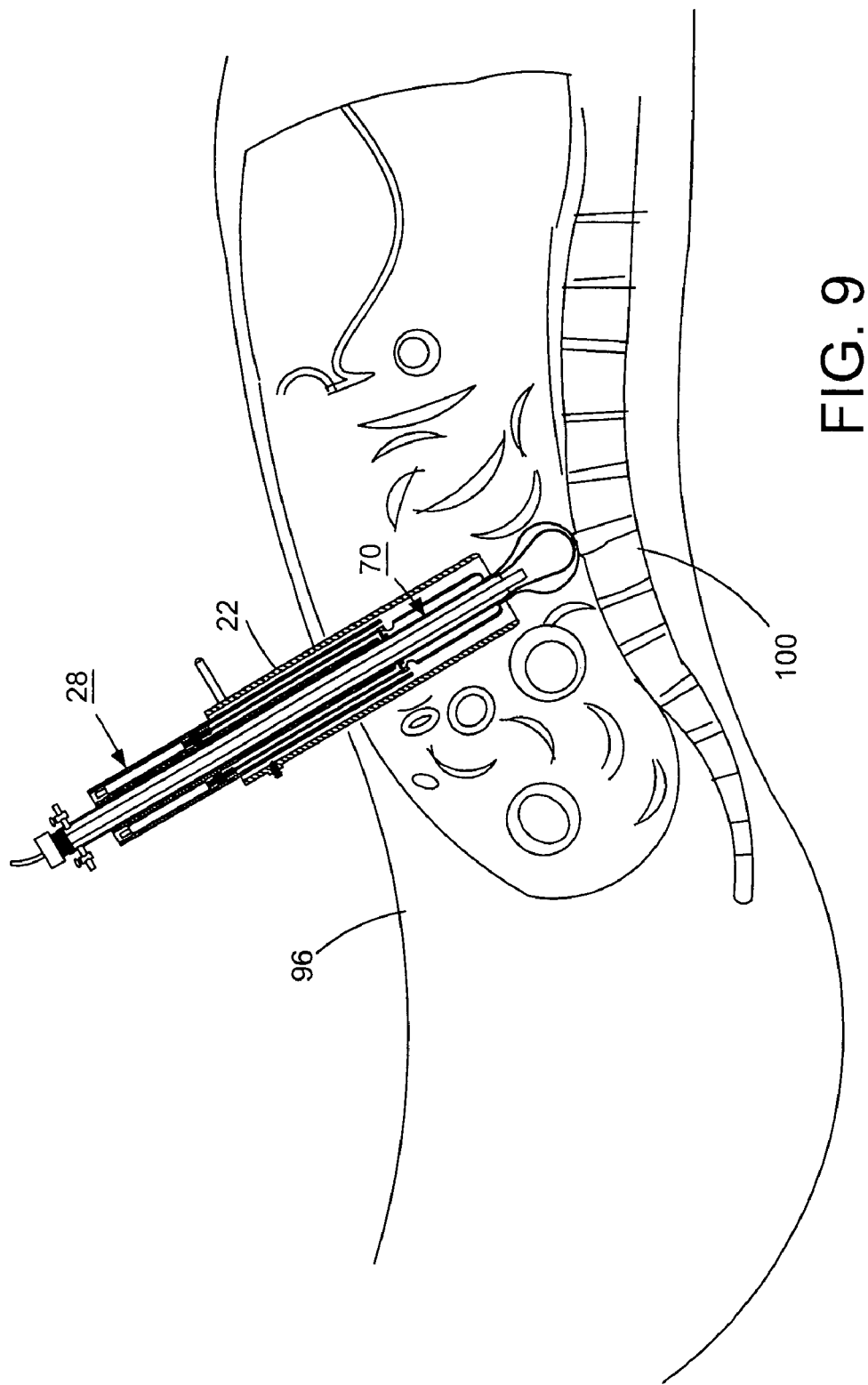
FIG. 9 is a schematic diagram showing the balloon carrying out a dissection of tissue.

As shown in FIG. 9, the cannula 22 is shown extending through an opening in the abdomen 96 of a patient 98, in a surgical operation on the patient's spine 100. The retractor 28 is shown positioned so that the retractor blades are inside the cannula 22, but the balloon dissector 70 protrudes through the distal opening of the cannula. The balloon is used to dissect tissue to gain access to the patient's spine, and is shown expanded by the introduction of fluid into its interior. The surgeon can observe the dissection visually on a monitor connected to the image transmitting device that extends into the interior of the balloon.

Figure 10:
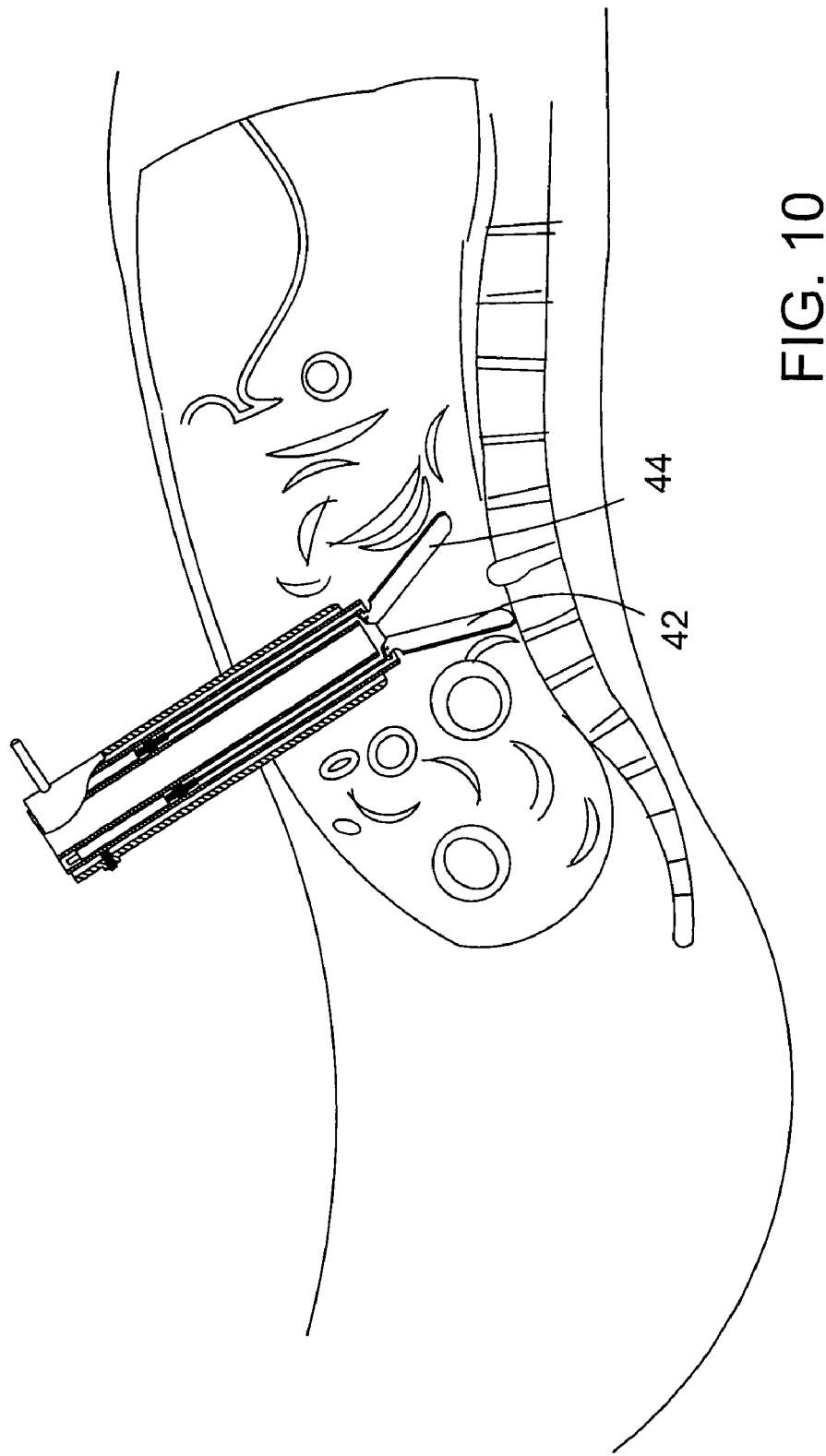
FIG. 10 is a schematic diagram, similar to FIG. 9, showing the retractor blades spreading tissue previously dissected by the balloon.

After completion of dissection by means of the balloon, the balloon is allowed to contract, by exhaustion of expansion fluid, to a size such that the retractor can be moved forward over the balloon without spreading the retractor blades. The balloon dissector can then be withdrawn, and the retractor blades 42 and 44 are then spread apart from each other as shown in FIG. 10. Since the blades are adjustable independently, they can be spread by adjustment of both blades, or by adjustment of either blade by itself. With the cannula rigidly supported on a support arm (not shown) and the retractor locked in place by the set screw 26 (FIG. 3), the surgeon can introduce other instruments through the central channel of the retractor, visualizing the surgical site, in this case the patient's spine, through another image transmitting device, which can extend through the retractor, or which can be introduced through another portal.

As will be apparent, the balloon dissector can be used to remove adhesions and dissect tissue for initial access to the surgical site, and the retractor blades can be used to expand and/or maintain the space opened up by dissection, to allow other surgical instruments to be introduced.

Various modifications can be made to the instrumentation described above. For example, although the retractor blades described herein are pivoted, as an alternative, linkage structures can be provided so that the retractor blades remain parallel to each other when expanding. The retractor blades can be formed in various shapes other than the shape illustrated, and the retractor can also have more than two blades. Moreover, although the retractor blades are preferably moved by a screw mechanism such as the mechanism shown in FIGS. 4 and 5, the blades can be controlled by various other mechanisms, such as a rack and pinion mechanism. The connection between an adjusting rod and a pivoted blade can be made by providing two balls on the rod, one ball being above, and the other being below, plate 66 (FIG. 4). The cross-sectional shape of the inner and outer tubes can be non-circular. For example, the tubes can be oval-shaped in transverse cross-section. The instruments can, of course, be made in various diameters and lengths.

Figure 11:
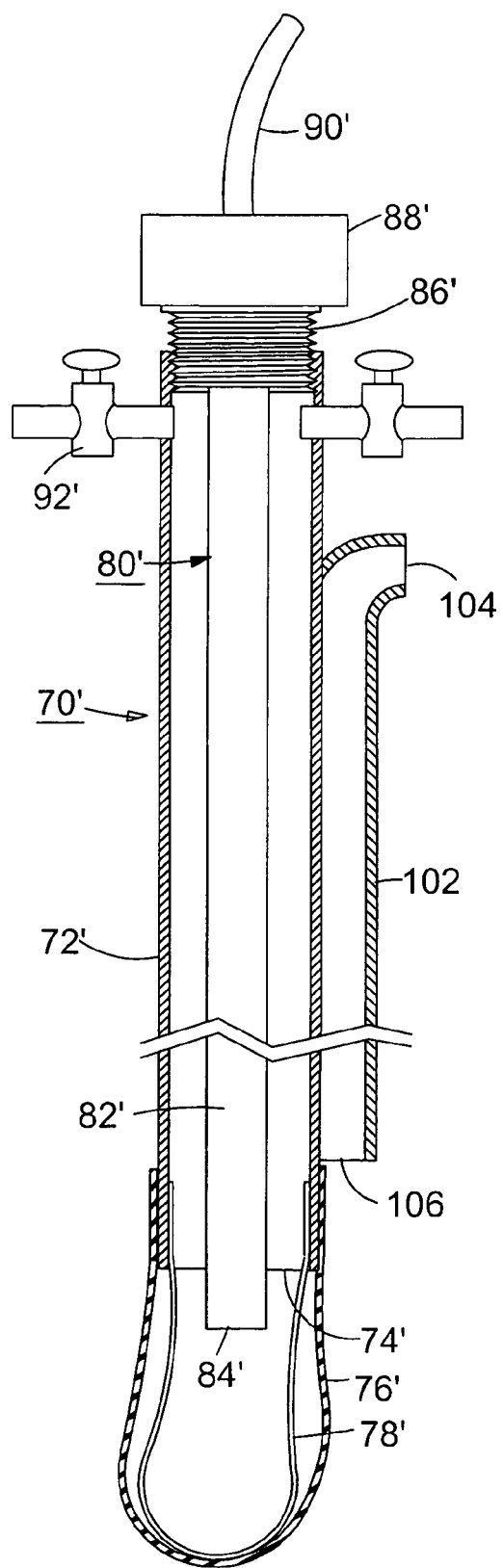
FIG. 11 is a shortened axial section, similar to FIG. 7, showing an elongated second tube having an auxiliary channel.

FIG. 11 shows a balloon dissector similar to that in FIG. 7. In FIG. 11, parts corresponding to those in FIG. 7 are identified by the same reference numbers followed by the prime (') symbol. As shown in FIG. 11, the balloon dissector can be provided with a wall 102 defining a separate working channel having a proximal opening 104 and a distal opening 106 adjacent to the balloon 76', and outside the balloon, for insertion of a variety of instruments, such as instruments for tissue resection, biopsy, or hemostasis. The separate working channel can also be used for introduction of saline solution to clean blood stains the exterior surface of the balloon so that they do not interfere with clear visualization by the surgeon. A rubber cap (not shown) can also be provided at the proximal end of the additional working channel so that saline solution can be injected under pressure. The separate working channel is preferably, but not necessarily, provided on the outside of the tube 72'. When the separate working channel is on the outside of the tube, the retractor blades should be positionable so that they are entirely within an axial projection of the retractor tube, but entirely outside an axial projection of the structure consisting of the tube 72' and the channel-defining wall 102 of the balloon dissector, so that the balloon dissector can pass between the blades before the blades are spread apart from each other.

Still other modifications may be made to the apparatus and method described above without departing from the scope of the invention as defined in the following claims.

What is claimed is:

1. An instrument for surgical dissection of tissue comprising:

an elongated tube having proximal and distal ends, the tube having an internal passage, extending along a central axis, for insertion of an instrument through the tube and a substantially cylindrical external surface symmetrical about said central axis;

plural retractor blades, each said blade extending in a distal direction from a location adjacent the distal end of the elongated tube and being pivoted for rotation about a pivot axis adjacent said distal end of the elongated tube, the pivot axis about which each of said blades is pivoted being disposed, at a fixed location relative to the distal end of the elongated tube, in a plane to which said central axis is perpendicular; and an adjuster rod connected to each blade at a connecting location spaced from the blade's pivot axis in a radial outward direction with respect to said central axis, each adjuster rod extending proximally at least part way through the elongated tube, and being accessible at a location adjacent the proximal end of the tube, said adjuster rods being movable longitudinally, restricted in their longitudinal movement to movement along axes of movement extending in parallel and fixed relation to said central axis, and movable along said axes of movement independently of one another for independent pivoting adjustment of each of said retractor blades about its pivot axis;

said blades having outer, tissue-engaging, surfaces which face in opposite directions and are convex throughout substantially their entire lengths in said distal direction in cross-sectional planes to which said distal direction is perpendicular, and having inner surfaces which are concave throughout substantially their entire lengths in said cross-sectional planes; and said blades are adjustable, by pivoting about said pivot axes, to positions in which they are all substantially within an axial projection of the substantially cylindrical external surface of the tube but substantially entirely external to an axial projection of said internal passage, and to positions in which parts of their outer, tissue-engaging, surfaces are external to said substantially cylindrical external surface.

2. An instrument according to claim 1, in which the plural retractor blades consist of two retractor blades in opposed relationship to each other.

3. An instrument according to claim 1 in which said internal passage is substantially symmetrical about said central axis.

4. An instrument according to claim 1, in which said adjusting rods have external helical screw threads threadingly engaged with internal helical screw threads fixed to said tube.

5. An instrument according to claim 4, in which said adjusting rods are separated from the internal passage by a second tube defining the internal passage.

6. An instrument for surgical dissection of tissue comprising:

an elongated first tube having proximal and distal ends, the tube having an internal passage for insertion of an instrument through the tube and a substantially cylindrical external surface substantially symmetrical about an axis of elongation, the internal passage being also substantially symmetrical about said axis;

two retractor blades in opposed relationship to each other, each said blade extending in a distal direction from a location adjacent the distal end of the elongated first tube and being pivoted for rotation about a pivot axis adjacent said distal end of the elongated first tube, the pivot axis about which each of said blades is pivoted being disposed, at a fixed location relative to the distal end of the elongated first tube, in a plane to which said axis of elongation is perpendicular;

an adjuster rod connected to each blade at a connecting location spaced from the blade's pivot axis in a radial outward direction with respect to said axis of elongation, each rod extending proximally at least part way through the elongated first tube, and being accessible at a location adjacent the proximal end of the tube, said adjuster rods being movable longitudinally, restricted in their longitudinal movement along axes of movement extending in parallel and fixed relation to said axis of elongation, and movable along said axes of movement independently of one another for independent pivoting adjustment of each of said retractor blades about its pivot axis; and a balloon dissector comprising an elongated second tube having proximal and distal ends, and an expandable balloon at the distal end of the second tube;

in which:

said blades having outer, tissue-engaging, surfaces which face in opposite directions and are convex throughout substantially their entire lengths in said distal direction in cross-sectional planes to which said distal direction is perpendicular, and having inner surfaces which face toward each other are concave throughout substantially their entire lengths in said cross-sectional planes; and the blades are adjustable, by pivoting about said pivot axes, to positions in which they are substantially within an axial projection of the substantially cylindrical external surface of the elongated first tube, but substantially entirely external to an axial projection of the second tube and to positions in which parts of their outer, tissue-engaging surfaces are external to said substantially cylindrical external surface; and the elongated second tube extends through the internal passage of the first elongated tube from a location proximal with respect to the proximal end of the first elongated tube to a location at which at least part of the expandable balloon is distal with respect to the blades;

whereby the balloon can be expanded to dissect tissue located in distal relation to the blades while said blades are substantially within an axial projection of the substantially cylindrical external surface of the elongated first tube, and then contracted to permit movement of the blades into a space created by the dissection of tissue by the balloon, whereby spreading of the tissue can be effected by adjustment of the blades to positions in which parts of their outer, tissue-engaging surfaces are external to said substantially cylindrical external surface, and, following withdrawal of the second elongated tube, another instrument can be introduced through the internal passage of the first tube for surgery on anatomical structure exposed by said dissection and spreading.

7. An instrument according to claim 6, in which the balloon is transparent, and including a shaft extending through the second elongated tube to a location within the balloon, the shaft comprising an image transmitter for transmitting a visual image of a patient's anatomical structure immediately external to the balloon, through the elongated first tube, to a location external to the patient.

8. An instrument according to claim 6, in which the balloon dissector has first passage, in said second tube, for a fluid used to expand the balloon, and a second passage, separate from the first passage, the second passage having a distal opening leading to a location external to the expandable balloon, whereby an instrument or irrigation fluid can be passed through the second passage.

9. An instrument according to claim 6, in which the balloon dissector has first passage, in said second tube, for a fluid used to expand the balloon, and a channel wall defining second passage, separate from the first passage, the second passage having a distal opening leading to a location external to the expandable balloon, whereby an instrument or irrigation fluid can be passed through the second passage, and in which the blades are adjustable to positions in which they are substantially within an axial projection of the substantially cylindrical external surface of the elongated first tube, but substantially entirely external to an axial projection of the second tube and said channel wall.

10. An instrument according to claim 6, in which the second tube is removable from the first tube.

11. An instrument according to claim 1, in which each said blade includes a pair of spaced plates at its connecting location, and each adjuster rod includes an element engaged with, and positioned between, a pair of said spaced plates whereby each blade can be made to pivot by axial movement of the adjuster rod connected thereto.

12. An instrument according to claim 4, in which said helical screw threads have a pitch sufficiently small to prevent the blades from being moved about their pivots by forces applied directly to the blades.

13. An instrument according to claim 6, in which each said blade includes a pair of spaced plates at its connecting location, and each adjuster rod includes an element engaged with, and positioned between, a pair of said spaced plates whereby each blade can be made to pivot by axial movement of the adjuster rod connected thereto.

14. An instrument according to claim 6, in which said adjusting rods have external helical screw threads threadingly engaged with internal helical screw threads fixed to said first tube.

15. An instrument according to claim 14, in which said helical screw threads have a pitch sufficiently small to prevent the blades from being moved about their pivots by forces applied directly to the blades.

* * * * *